United States Patent [19]
Sela et al.

[11] Patent Number: 5,939,603
[45] Date of Patent: Aug. 17, 1999

[54] PLANTS TRANSFORMED WITH A POTATO VIRUS Y GENE

[75] Inventors: Ilan Sela, Nes Ziona; Eyal Vardi, Rehovot; Yehuda Stram, Bat Yam, all of Israel

[73] Assignee: Yissum Research Development Company of Hebrew University of Jerusalem, Israel

[21] Appl. No.: 08/199,485

[22] Filed: Feb. 22, 1994

[30] Foreign Application Priority Data

Feb. 23, 1993 [IL] Israel ........................................ 104830

[51] Int. Cl.$^6$ ............................... A01H 5/00; C12N 5/04; C12N 15/82
[52] U.S. Cl. ................... 800/301; 435/252.3; 435/320.1; 435/419; 435/468; 435/471
[58] Field of Search ..................................... 800/205, 250, 800/298, 301, 280; 435/69.1, 172.3, 240.4, 320.1, 252.3, 252.33, 419, 418, 468, 471; 536/23.72

[56] References Cited

U.S. PATENT DOCUMENTS 5,589,612  12/1996  Jilka et al. ............................... 800/205

OTHER PUBLICATIONS

Nejidat et al (1990) Physiologia Plantarium 80: 662–668.
Maiti et al (1993) Proc. Natl Acad Sci USA 90: 6110–6114.
Braun et al (1992) The Plant Cell 4: 735–744.
Stark et al (1989) Bio/Technology 7: 1257–1262.
Robaglia et al (1989) J Gen. Virol 70: 935–947.

*Primary Examiner*—Elizabeth F. McElwain
*Attorney, Agent, or Firm*—Kohn & Associates

[57] ABSTRACT

The invention relates to chimeric plasmids comprising at least one non-structural potyvirus gene or fragment thereof, which gene is capable of being expressed in a plant transformed with the chimeric plasmid, the thus transformed plant being resistant to an infection by a plant potyvirus.

The invention also relates to vectors comprising a chimeric plasmid according to the invention, particularly microorganisms transformed with the chimeric plasmids of the invention.

Potyvirus-resistant plants having cells containing in their genomes the chimeric DNA sequences according to the invention, as well as seeds and cells of a potyvirus-resistant plant containing in their genome the said chimeric DNA sequences are also described and claimed, as well as methods of protecting plants against potyvirus infection wherein genomes of cells of the plant are provided with a chimeric DNA sequence according to the invention, whereby the calls become resistant to an infection by a potyvirus.

26 Claims, 4 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 1479 base pairs
        (B) TYPE: nucleic acid
        (C) STRANDEDNESS: single
        (D) TOPOLOGY: linear     (ii) MOLECULE TYPE: DNA (genomic)

(ix) FEATURE:
        (A) NAME/KEY: misc_feature
        (B) LOCATION: 1..15
        (D) OTHER INFORMATION: /note= "Synthetic sequence with
            restriction sites and ribosome binding sites which
            were artificially ligated to the viral sequences."

(ix) FEATURE:
        (A) NAME/KEY: misc_feature
        (B) LOCATION: 1465..1479
        (D) OTHER INFORMATION: /note= "Synthetic sequence with
            restriction sites and ribosome binding sites which
            was artificially ligated to the viral sequence."

(xi) SEQUENCE DESCRIPTION: SEQ ID NO:1:

```
CTAGACAATG GTTAAGGAAT TCTTCGGATC TGCATACAGG AAAAAGGGAA AAGGTAAAGG      60

TACCACAGTT GGTATGGGTA AGTCAAGCAG GAGGTTCATC AACATGTATG GGTTTGATCC     120

AACAGAGTAC TCATTCATCC AATTCGTTGA TCCACTCACT GGGCGGCAAA TAGAAGAAAA     180

TGTCTATGCT GACATTAGAG ATATTCAAGA GAGATTTAGT GAAGTGCGAA AGAAAATGGT     240

TGAGAATGAT GACATTGAAA TGCAAGCCTT GGGTAGTAAC ACGACCATAC ATGCATACTT     300

CAGGAAAGAT TGGTGTGATA AAGCTTTGAA GATTGATTTA ATGCCACATA ACCCACTCAA     360

AGTTTGTGAC AAAACAAATG GCATTGCCAA ATTTCCTGAG AGAGAGCTCG AACTAAGGCA     420

GACTGGGCCA GCTGTAGAAG TCGATGTGAA GGACATACCA GCACAGGAGG TGGAGCATGA     480

AGCTAAATCG CTCATGAGAG GCTTGAGAGA CTTCAACCCA ATTGCCCAAA CAGTTTGTAG     540

GCTGAAAGTA TCTGTTGAAT ATGGGGCATC AGAGATGTAC GGTTTTGGAT TTGGAGCATA     600

CATAGTAGCG AACCACCATT TATTTAGGAG TTACAATGGT TCCATGGAGG TGCAATCCAT     660

GCACGGTACA TTCAGGGTGA AGAATCTACA CAGTTTGAGC GTTCTGCCAA TTAAAGGTAG     720

GGACATCATC CTCATCAAAA TGCCGAAAGA TTTCCCTGTC TTTCCACAGA AATTGCATTT     780

CCGAGCTCCT ACACAGAATG AAAGAATTTG TTTAGTTGGA ACCAACTTCC AAGAGAAGTA     840

TGCTTCGTCG ATCATCACAG AAACAAGCAC TACTTACAAT ATACCAGGCA GCACATTCTG     900
```

```
GAAGCATTGG ATTGAAACAG ATAATGGACA TTGTGGACTA CCAGTGGTGA GCACCGCCGA    960

TGGATGTATA GTCGGAATTC ACAGTCTGGC AAACAATGCA CACACCACGA ACTACTACTC   1020

AGCCTTCGAT GAAGATTTTG AAAGCAAGTA CCTCCGAACC AATGAGCACA ATGAATGGGT   1080

CAAGTCTTGG GTTTATAATC CAGACACAGT GTTGTGGGGC CCGTTGAAAC TTAAAGACAG   1140

CACTCCCAAA GGGTTATTCA AAACAACAAA GCTTGTGCAA GATCTAATCG ATCATGATGT   1200

AGTGGTGGAG CAAGCTAAGC ATTCTGCATG GATGTTTGAA GCCTTGACAG GAAATTTGCA   1260

AGCTGTCGCA ACAATGAAGA GCCAATTAGT AACCAAGCAT GTAGTTAAAG GAGAGTGTCG   1320

ACACTTCACA GAATTTCTGA CTGTGGATGC AGAGGCAGAG GCAGAGGCAT TCTTCAGGCC   1380

TTTGATGGAT GCGTATGGGA AAAGCTTGCT AAATAGAGAT GCGTACATCA AGGACATAAT   1440

GAAGTATTCA AAACCTATAG ATGTAATTCC ATTGTGATC                         1479
```

(2) INFORMATION FOR SEQ ID NO:2:

(i) SEQUENCE CHARACTERISTICS:
        (A) LENGTH: 3923 base pairs
        (B) TYPE: nucleic acid
        (C) STRANDEDNESS: single
        (D) TOPOLOGY: linear     (ii) MOLECULE TYPE: DNA (genomic)

(ix) FEATURE:
        (A) NAME/KEY: misc_feature
        (B) LOCATION: 1..15
        (D) OTHER INFORMATION: /note= "Synthetic sequences with
            restriction sites and ribosome binding sites which
            were artificially ligated to the viral sequence."

(ix) FEATURE:
        (A) NAME/KEY: misc_feature
        (B) LOCATION: 3909..3923
        (D) OTHER INFORMATION: /note= "Synthetic sequences with
            restriction sites and ribosome binding sites which
            were artificially ligated to the viral sequence."

(xi) SEQUENCE DESCRIPTION: SEQ ID NO:2:

```
CTAGACAATG GTTAAGGAAT TCTTCGGATC TGCATACAGG AAAAAGGGAA AAGGTAAAGG    60

TACCACAGTT GGTATGGGTA AGTCAAGCAG GAGGTTCATC AACATGTATG GGTTTGATCC   120

AACAGAGTAC TCATTCATCC AATTCGTTGA TCCACTCACT GGGCGGCAAA TAGAAGAAAA   180

TGTCTATGCT GACATTAGAG ATATTCAAGA GAGATTTAGT GAAGTGCGAA AGAAAATGGT   240

TGAGAATGAT GACATTGAAA TGCAAGCCTT GGGTAGTAAC ACGACCATAC ATGCATACTT   300

CAGGAAAGAT TGGTGTGATA AGCTTTGAA GATTGATTTA ATGCCACATA ACCCACTCAA   360

AGTTTGTGAC AAAACAAATG GCATTGCCAA ATTTCCTGAG AGAGCTCG AACTAAGGCA   420

GACTGGGCCA GCTGTAGAAG TCGATGTGAA GGACATACCA GCACAGGAGG TGGAGCATGA   480

AGCTAAATCG CTCATGAGAG GCTTGAGAGA CTTCAACCCA ATTGCCCAAA CAGTTTGTAG   540

GCTGAAAGTA TCTGTTGAAT ATGGGCATC AGAGATGTAC GGTTTTGGAT TGGAGCATA   600

CATAGTAGCG AACCACCATT TATTTAGGAG TTACAATGGT TCCATGGAGG TGCAATCCAT   660

GCACGGTACA TTCAGGGTGA AGAATCTACA CAGTTTGAGC GTTCTGCCAA TTAAAGGTAG   720

GGACATCATC CTCATCAAAA TGCCGAAAGA TTTCCCTGTC TTTCCACAGA AATTGCATTT   780

CCGAGCTCCT ACACAGAATG AAAGAATTTG TTTAGTTGGA ACCAACTTCC AAGAGAAGTA   840

TGCTTCGTCG ATCATCACAG AAACAAGCAC TACTTACAAT ATACCAGGCA GCACATTCTG   900

GAAGCATTGG ATTGAAACAG ATAATGGACA TTGTGGACTA CCAGTGGTGA GCACCGCCGA   960

TGGATGTATA GTCGGAATTC ACAGTCTGGC AAACAATGCA CACACCACGA ACTACTACTC  1020
```

```
AGCCTTCGAT GAAGATTTTG AAAGCAAGTA CCTCCGAACC AATGAGCACA ATGAATGGGT    1080

CAAGTCTTGG GTTTATAATC CAGACACAGT GTTGTGGGGC CCGTTGAAAC TTAAAGACAG    1140

CACTCCCAAA GGGTTATTCA AAACAACAAA GCTTGTGCAA GATCTAATCG ATCATGATGT    1200

AGTGGTGGAG CAAGCTAAGC ATTCTGCATG GATGTTTGAA GCCTTGACAG GAAATTTGCA    1260

AGCTGTCGCA ACAATGAAGA GCCAATTAGT AACCAAGCAT GTAGTTAAAG GAGAGTGTCG    1320

ACACTTCACA GAATTTCTGA CTGTGGATGC AGAGGCAGAG GCAGAGGCAT TCTTCAGGCC    1380

TTTGATGGAT GCGTATGGGA AAAGCTTGCT AAATAGAGAT GCGTACATCA AGGACATAAT    1440

GAAGTATTCA AAACCTATAG ATGTTGGTGT CGTGGATCGG ATGCATTTGA GGAAGCCATC    1500

AATAGGGTTA TCATCTACCT GCAATGTGCA CGGCTTCAAG AAGTGTGCAT ATGTCACTGA    1560

TGAGCAAGAA ATTTTCAAAG CGCTCAACAT GAAAGCTGCA GTCGGAGCCA GTTATGGGTG    1620

CAAAAAGAAA GACTATTTTG AGCATTTCAC TGATGCAGAT AAGGAAGAAA TAGTCATGCA    1680

AAGCTGTCTG CGATTGTATA AAGGTTTGCT TGGCATTTGG AACGGATCAT TGAAGGCAGA    1740

GCTCCGGTGT AAGGAGAAGA TACTTGCAAA TAAGACGAGG ACGTTCACTG CTGCACCTCT    1800

AGACACTTTG CTGGGTGGTA AAGTGTGTGT TGATGACTTC AATAATCAAT TTTATTCAAA    1860

GAATATTGAA TGCTGTTGGA CAGTTGGGAT GACTAAGTTT TATGGTGGTT GGGATAAACT    1920

GCTTCGGCGT TTACCTGAGA ATTGGGTATA CTGTGATGCT GATGGCTCAC AGTTTGATAG    1980

TTCACTAACT CCATACCTAA TCAATGCTGT TCTCACCATC AGAAGCACAT ACATGGAAGA    2040

CTGGGATGTG GGGTTGCAGA TGCTGCGCAA TTTATACACT GAGATTGTTT ACACACCAAT    2100

TTCAACTCCA GATGGAACAA TTGTCAAGAA GTTTAGAGGT AATAATAGTG GTCAACCTTC    2160

TACCGTTGTG GATAATTCTC TCATGGTTGT CCTTGCTATG CATTACGCTC TCATTAAGGA    2220

GTGCGTTGAG TTTGAAGAAA TCGACAGCAC GTGTGTATTC TTTGTTAATG GTGATGACTT    2280

ATTGATTGCT GTGAATCCGG AGAAAGAGAG CATTCTCGAT AGAATGTCAC AACATTTCTC    2340

AGATCTTGGT TTGAACTATG ATTTTTCGTC GAGAACAAGA AGGAAGGAGG AATTGTGGTT    2400

CATGTCCCAT AGAGGCCTGC TAATCGAGGG TATGTACGTG CCAAAGCTTG AAGAAGAGAG    2460

AATTGTATCC ATTCTGCAAT GGGATAGAGC TGATCTGCCA GAGCACAGAT TAGAAGCGAT    2520

TTGCGCAGCT ATGATAGAGT CCTGGGGTTA TTCTGAACTA ACACACCAAA TCAGGAGATT    2580

CTACTCATGG TTATTGCAAC AGCAACCTTT TGCAACAATA GCGCAGGAAG GGAAGGCTCC    2640

TTATATAGCA AGCATGGCAC TAAGGAAACT GTATATGGAT AGGGCTGTGG ATGAGGAAGA    2700

GCTAAGAGCC TTCACTGAAA TGATGGTCGC ATTAGATGAT GAGTTTGAGC TTGACTCTTA    2760

TGAAGTACAC CATCAAGCAA ATGACACAAT TGATGCAGGA GGAAGCAACA AGAAAGATGC    2820

AAAACCAGAG CAGGGCAGCA TCCAGCCAAA CCCGAACAAA GGAAAGGATA AGGATGTTAA    2880

TGCAGGCACA TCTGGGACAC ATACTGTGCC GAGAATCAAG GCTATCACGT CCAAAATGAG    2940

AATGCCCACA AGCAAGGGAG CAACCGTGCC AAACTTAGAA CATTTGCTTG AGTATGCTCC    3000

ACAACAAATT GATATTTCAA ATACTCGGGC AACTCAATCA CAGTTTGATA CGTGGTATGA    3060

GGCAGTGCGG ATGGCATACG ACATAGGAGA AACTGAGATG CCAACTGTGA TGAATGGGCT    3120

TATGGTTTGG TGCATTGAAA ATGGAACCTC GCCAAATGTC AACGGAGTTT GGGTTATGAT    3180

GGATGGGAAT GAACAAGTTG AGTACCCGTT GAAACCAATC GTTGAGAATG CAAAACCAAC    3240

CCTTAGGCAA ATCATGGCAC ATTTCTCAGA TGTTGCAGAA GCGTATATAG AAATGCGCAA    3300

CAAAAAGGAA CCATATATGC CACGATATGG TTTAATTCGA AATCTGCGGG ATATGGGTTT    3360

AGCGCGTTAT GCCTTTGACT TTTATGAGGT CACATCACGA ACACCAGTGA GGGCTAGGGA    3420
```

```
AGCGCACATT CAAATGAAGG CCGCAGCATT GAAATCAGCC CAACCTCGAC TTTTCGGGTT     3480

GGACGGTGGC ATCAGTACAC AAGAGGAGAA CACAGAGAGG CACACCACCG AGGATGTCTC     3540

TCCAAGTATG CATACTCTAC TTGGAGTCAA GAACATGTGA TGTAGTGTCT CTCCGGACGA     3600

TATATAAGTA TTTACATATG CAGTAAGTAT TTTGGCTTTT CCTGTACTAC TTTTATCATA     3660

ATTAATAATC GTTTGAATAT TACTGGCAGA TAGGGGTGGT ATAGCGATTC CGTCGTTGTT     3720

AGTGACCTTA GCTGTCGGTT CTGTATTATT AAGTCTTAGA TAAAAAGTGC CGGGTTGTTG     3780

TTGTGTGACT GATCTATCGA TTAGGTGATG CTGTGATTCT GTCATAGCAG TGACTATGTC     3840

TGGATTTAGT TACTTGGGTG ATGCTGTGAT TCTGTCATAG CAGTGACTGT AAACTTCAAT     3900

CAGGAGACAA TTCCATTGTG ATC                                            3923

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:3:

CTATCCTTCG CAAGACCCTT C                                              21

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:4:

TTTGGATCTG CATACAGGAA GAAAGGG                                        27

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:5:

CCGACTATAC ATCCATCGGC GGTG                                           24
```

PLANTS TRANSFORMED WITH A POTATO VIRUS Y GENE

FIELD OF THE INVENTION

The invention relates to plants transformed with a potato virus Y non-structural gene which are resistant to infection by the plant potyviruses.

BACKGROUND OF THE INVENTION

Potyviruses constitute the largest known group of plant viruses, infecting a wide variety of plants, inter alia, potato, tomato, tobacco and pepper. Potyviruses thus inflict heavy economic damage [Hollings, M. & Brunt, A. A. (1981) in Handbook of Plant Virus Infections: Comparative Diagnosis, ed. Kurstak, E. (Elsevier/North Holland), pp. 731–807; Dougherty, W. G. & Carrington, J. C. (1988) Ann. Rev. Phytopathol. 26:123–143]. The organization of the large (9–10 Kb) RNA genome of potyviruses is well understood. One of their major characteristics is that their genome comprises a single, large, open reading frame, encoding a large primary polyprotein. The mature virus-encoded proteins are produced by self-proteolysis, carried out by the products of three of the viral cistrons [Verchot, J., et al., (1991) Virology 185:527–535; Hellmann, G. M., et al., (1988) Virology 163:554–562; Carrington, J. C., et al., (1989) EMBO J. 8:365–370; Carrington, J. C., et al., (1988) J. Virol. 62:2313–2320; Garcia, J. A., et al., (1989) virology 170:362–369; Carrington, J. C. & Herndon, K. L. (1992) Virology 187:308–315]. Several non-structural viral proteins tend to accumulate in infected tissues, some in the form of inclusion bodies [[Dougherty & Carrington, 1988] Matthews, R. E. F. (1991). Plant Virology ($3^{rd}$ edition), Academic Press, San Diego]. The nuclear inclusion body comprises aggregates of two virus-encoded proteins: NIa and NIb. NIa is the major potyvirus protease, cleaving at all proteolytic sites except the first two in the N-terminal region. [Dougherty and Carrington, 1988; Hellmann et al., 1988; Garcia et al., 1989]. NIb is thought to be associated with replication, due to some sequence homology with the polio replicase [Allison, R., et al., (1986) Virology 154:9–20; Domier, L. L., et al., (1987) Virology 158:20–27; Robaglia, C., et al., (1989) J. Gen. Virol. 70:935–947].

Plants transformed with viral structural gene sequences have been shown to acquire resistance to infection by the same, or related viruses [reviewed in Beachy, R. N., et al., (1990) Annual Rev. Phytopatol. 28:451–474]. Resistance has also been recently reported for the first time in tobacco transformed with a nonstructural viral sequence, the putative tobacco mosaic virus replicase [Golemboski, et al., (1990) Proc. Natl. Acad. Sci. USA 87:6311–6315].

Potyviruses express a fair amount of nonstructural viral proteins that aggregate into stable forms and thus offer a unique opportunity to study the expression and function of these proteins. In the course of studying the factors controlling NIa expression and function, the inventors transformed plants with the NIa cistron. Surprisingly, these transformed plants exhibited a high degree of resistance to potyvirus infection.

SUMMARY OF THE INVENTION

The invention relates to a chimeric plasmid comprising at least one non-structural potyvirus gene or fragment thereof, which gene is capable of being expressed in a plant transformed with the chimeric plasmid, the thus transformed plant being resistant to an infection by a plant potyvirus.

More particularly, the invention relates to a chimeric plasmid comprising at least one potyvirus non-structural gene, which potyvirus gene encodes a potyvirus protease, or a potyvirus protease, in combination with replicase and coat protein.

In addition to said potyvirus non-structural gene or fragments thereof, the chimeric plasmids of the invention comprise a suitable plasmid, preferably a binary plasmid, and optionally further comprise at least one genetic control element, selected from the group consisting of promoters, enhancers, terminators and other signal elements improving translation and transcription and DNA sequences required for the insertion of foreign DNA into the plant genome.

The invention also relates to vectors comprising a chimeric plasmid according to the invention. The vectors according to the invention are preferably microorganisms transformed with the chimeric plasmids of the invention. A preferred vector according to the invention is an Agrobacterium transformed with the chimeric plasmids of the invention.

In addition, the invention relates to potyvirus-resistant plants having cells containing in their genomes the chimeric DNA sequences according to the invention, as well as seeds and cells of a potyvirus-resistant plant containing in their genome the said chimeric DNA sequences.

The invention also relates to a plant cell culture consisting of cells according to the invention.

Within the scope of the invention are also methods of protecting plants against potyvirus infection wherein genomes of cells of the plant are provided with a chimeric DNA sequence according to the invention, whereby the cells become resistant to an infection by a potyvirus.

BRIEF DESCRIPTION OF THE FIGURES

FIG. 1 Maps of the binary vectors pG3PVY3.9 and pGNIa1.4. The PVY sequences were inserted between the cauliflower mosaic virus 35S promoter and the transcription-termination signal of gene 7 of pTiA6 [An, G., et al., (1989) in Plant Molecular Biology Manual eds. Gelvin, S. B. & Schilperoot, R. A. A3: pp. 1–9]. The sequence at the top of each illustration is that of a translation-initiation signal ligated to PVY clone. Numbers indicate the base number in the PVY sequence [Robaglia et al., 1989]. NPTII: the gene for neomycine phospho-transferase II. BR and BL: The right and left border sequences of T-DNA.

A: The alignment of primers with the inserted PVY1.4NIa. Primer #1 aligns with the promoter which is not transcribed to RNA. Primer sequences are given in the following examples.

B: A sample of a Southern blot of the PCR product of transgenic (V2, V3) plants and of a non-transformed (SR1) plant.

Lanes 1 & 2: DNA-PCR of V2 using primers #1 (specific for DNA only) and #11, or #10 and #11, respectively.

Lanes 3 & 4: RNA-PCR of V2 using primers #10 and #11, or #1 and #11, respectively.

Lane 5: Stained size markers (not seen in the autoradiogram).

Lanes 6 & 7 and 8 & 9: RNA-PCR as in lanes 3 & 4 —but with V3 or the non-transformed SR1 plants, respectively. Arrows indicate the position of the respective bands.

FIG. 3 Demonstration of resistance to PVY. The plants were inoculated with 30 µg/ml PVY. The plant on the left was transformed with pGNIa1.4 carrying the cistron for a PVY protease (NIa). The plant on the right is a control, transformed by the insert-less vector pGA643. Plants are shown 20 days post-inoculation.

A. pGNIa1.4-transformed plants. The control curve represents data obtained from plants transformed by the insert-less vector pGA643. Control curves obtained from non-transformed plants and $NIa^-$ plants were similar. V2 and V3 represent PVY accumulation in four to five $R_1$ transformed, fully resistant plants.

B. pG3PVY3.9-transformed plants. I10 and I33 represent average values in four $R_1$ resistant plants. I33e is an $R_2$ plant derived from I33 which showed only partial resistance.

C. PVY titer in transgenic plants following exposure to 35° C. Samples were taken 20 days post inoculation. V3c and V3j are resistant pGNIa1.4-transformed plants (derivatives of V3 in A). I10c is a pG3PVY3.9-transformed resistant plant (a derivative of I10 in B). I1j is an R2 plant, a progeny of a non-resistant pG3PVY3.9-transformed parent. VII7 is a non-resistant plant transformed by the insert-less vector pGA643.

FIG. 5 Western blot analysis of the processing of the PVY polyprotein in pG3PVY3.9-transformed plants. Protein (50 μg/lane) extracted from transgenic, or PVY-infected, tobacco leaves and was electrophoresed, blotted, reacted with antibodies to PVY-CP and subjected to autoradiography. Two gels were run in parallel. The left blot was subjected to a longer exposure than the right one. The extracts in the various lanes were as follows:

Lane 1: Tobacco leaves transformed with the insert-less vector pGA643.

Lanes 2,3,4,5,10,11: Leaves from various transgenic tobacco plants.

Lanes 7 & 8: PVY-infected leaves.

Lanes 6 & 9: Size markers (only the 30KDa marker reacted with antibody and is seen on the autoradiogram).

The position and size of protein bands reacting specifically with the PVY-CP antibody are marked at the left margin.

DETAILED DESCRIPTION OF THE INVENTION

The present invention relates to a chimeric plasmid comprising at least one non-structural potyvirus gene or fragment thereof, which gene is capable of being expressed in a plant transformed with the chimeric plasmid, the thus transformed plant being resistant to an infection by a plant potyvirus.

The chimeric plasmids according to the invention preferably comprise a potyvirus non-structural gene which encode a potyvirus protease, or a fragment thereof, or potyvirus non-structural DNA sequence encoding protease, replicase and coat protein, or fragments thereof.

One preferred such viral INA sequence, designated NIa1.4 (SEQ ID NO: 1), which consists of bases 5812–7260 of the potyvirus Y genome, that is all but the first 100 5'-terminal bases of the cistron encoding NIa potyvirus Y protease, as well as the first 251 bases of the next cistron NIb.

Another preferred viral DNA sequence, desiganted 3'PVY3.9 (SEQ ID NO: 2), carries the above NIa sequence, the NIb protease sequence and the CP coat protein sequence. This sequence consists of bases 5812–9704 of the potato virus Y genome, that is the last three cistrons of the genome.

In addition to the potyviral DNA, a chimeric plasmid according to the invention comprises a suitable plasmid in which said viral DNA can replicate, and preferably also comprise at least one plant control element, selected from the group consisting of promotors, enhancers, terminators and other signal elements improving translation and transcription or required for the insertion of foreign DNA into the plant DNA.

The plasmid can be any suitable commercially available plasmid. For example, a suitable plasmid would be one enabling replication of the potyvirus DNA in *E. coli*. One such plasmid is the commercially available pBluescript KS (Stratagene).

Preferred plasmids for constructing the chimeric plasmids of the invention are suitable binary plasmids, comprising at least one plant control element, selected from the group consisting of promotors, enhancers, terminators and other signal elements improving translation and transcription or required for the insertion of foreign recombinant DNA into the plant DNA.

Preferably, the binary plasmid comprises a plant promotor region and two tandem nos termination signals in opposite orientation.

One such suitable binary plasmid is the plasmid pGA643.

A preferred chimeric plasmid according to the invention comprises said potyvirus NIa1.4 sequence (SEQ ID NO: 1), inserted at the XbaI site of the binary plasmid pGA643.

Another preferred chimeric plasmid according to the invention comprises said potyvirus 3'PVY3.9 sequence (SEQ ID NO: 2), inserted between the XbaI and BglII sites of the binary plasmid pGA643.

The invention also relates to vectors comprising a chimeric plasmid according to the invention. Preferably, a vector according to the invention comprises a microorganism transformed with said chimeric plasmid. A preferred vector according to the invention is E. coli, transformed with a chimeric plasmid according to the invention. Such transformed *E. coli* may be subsequently used to transform other microorganisms, preferably Agrobacterium, with the chimeric plasmids of the invention. Thus, a most preferred vector according to the invention is an Agrobacterium transformed with the chimeric plasmids of the invention. *Agrobacterium tumafaciens* is the most preferred Agrobacterium.

The invention also relates to a potyvirus-resistant plant having cells containing in their genomes the chimeric DNA sequences according to the invention, preferably said preferred chimeric plasmids. Also within the scope of the invention are seeds of a potyvirus resistant plant containing in their genome the chimeric DNA sequences according to the invention as well as other plant cells containing in their genome said chimeric sequences.

The invention also relates to a plant cell culture consisting of cells according to the invention.

In addition, the invention relates to methods of protecting plants against potyvirus infection wherein genomes of cells of the plant are provided with a chimeric DNA sequence according to the invention, whereby the plants become resistant to an infection by a potyvirus.

As will be shown in the following Examples, the present invention relates to resistance of plant to potyvirus infection by transforming the plants with non-structural viral genes. While transformation of plants with a non-structural tobacco mosaic virus coding for a TMV replicase has been reported recently, as stated above, the present inventors have surprisingly found that tranformation of plants with genes encoding proteins with different viral functions, i.e. protease, or protease and coat protein, and from a different viral origin, potyvirus, renders the plants resistant to infection by potyvirus.

The original transformed plants were propagated by self-pollination for two generations, and most of the $R_2$ plants maintained their resistance. About 180 transformed R1 plants were checked for resistance, out of which five were found to be partially resistant (e.g. a delayed infection was noted) and four were fully resistant (failing to support infection for 50 days). The copy number of the inserted NPTII gene could be determined from the segregation pattern for Km (kanamycin) resistance. Although the NIa sequences were linked to this gene, segregation for $Km^+$ is only indicative (but not conclusive) of the copy number of NIa sequences, since many cases of sequence "escapes" have been recorded [Wimmer, 1982]. However, as an arbitrary starting point, the two transgenic lines (V2 and V3), presumed to carry two copies of the NIa gene, were included in the first sample taken for a study of resistance. As indicated in Table 1 below, all 10 $R_1$ progeny of these plants exhibited some degree of resistance, ranging from delayed symptom appearance (and much milder symptoms), to total resistance throughout the 50-day experimental period (in about 50% of the cases). Line V6 on the other hand, carrying a single copy of the insert, exhibited only a short delay in symptom appearance, and could not be considered resistant. However, the sample sizes were too small to validate the necessity of a higher copy number in obtaining the observed resistance.

Only a small proportion of the transformed plants exhibited protection. It is, therefore, possible that during the cloning manipulations, some slight accidental DNA modification took place causing a few individual plants to express inactive PVY protease, thereby becoming resistant.

Several other observations regarding nonstructural viral genes are in line with this postulation. Plants transformed with the gene for the 54-KDa replicase read-through protein of TMV became resistant [Wimmer, 1982], as did those with the read-through replicase of pea early browning virus [MacFarlane, S. A. & Davies J. W. (1992) Proc. Natl. Acad. Sci. USA 89:5829–5833]. Anderson et al. [Anderson, J. M., et al., (1992) Proc. Natl. Acad. Sci. USA 89:8759–8763 ]showed resistance in plants transformed with an inactive, truncated cucumber mosaic virus replicas sequence. This phenomenon supports the above-mentioned hypothesis that resistance conferred by nonstructural viral genes might result from overexpression of the defective viral protein, defined as "dominant negative mutation" by Herskowitz [Herskowitz, I. (1987) Nature 329:219–222].

As shown in the examples, the NIa-transgenic plants maintain a significant degree of resistance after a considerable increase in temperature for relatively long periods.

Preferred embodiments of the invention will be described in more detail on hand of the following examples (in which potato virus Y is desiganted PVY), which are illustrative only and do not limit the scope of the invention which is only defined by the appended claims.

EXAMPLES

Materials and Methods

Plant transformation and selection.

Plants were transformed with two PVY-cDNA constructs (described in detail below): NIa1.4 (SEQ ID NO: 1) carrying most of the NIa (a protease cistron) sequence, and 3'PVY3.9 (SEQ ID NO: 2) carrying the above NIa sequence, the NIb and coat protein (CP) cistrons and the 3' non-coding region of PVY. These PVY sequences were placed in the binary plasmid pGA643 [13]. The chimeric plasmids were transferred to *Agrobacterium tumefaciens* (EHA 101). Tobacco (*Nicotiana tabacum* cv. SR1) leaf disks were inoculated with the transformed Agrobacterium [Horsch, R. B., et al., (1985) Science 227:1229–1231], and maintained on a regeneration medium containing Murashige and Skoog (MS) salt mixture [Murashige, T. & Skoog, F. (1962) Physiol. Plant. 15:485-], 2% sucrose, 1% mannitol, 1% Noble agar, 2 mg/l zeatin and 0.1 mg/l indole acetic acid, pH 5.8, supplemented with 300 μg/ml kanamycin (Km). Shoots that developed under these conditions were transferred individually to tissue-culture flasks containing MS salts, 3% sucrose, 1% Noble agar and 400 μg/ml Km. Rooted plantlets were transplanted in autoclaved soil and grown in a greenhouse. All stages were carried out at 24°–26° C.

The primary transformed plants were designated the $R_0$ generation. Selected $R_0$ plants (see below for selection criteria) were self-pollinated, and their seeds were collected and germinated on Km-containing agar. The resultant $R_1$ generation segregated for Km-sensitivity or Km-resistance. The Km-resistant plantlets were kept for further studies, as well as a Km-sensitive specimen which served as a negative control for each transformation event. $R_1$ plants were also self-pollinated and $R_2$ plants were treated and selected as above. The copy number of the inserted neomycine phosphotransferase II (NPTII; $Km^+$) gene was determined from the $R_1$ segregation, and the NPTII homozygotic state was determined from the segregation of $R_2$.

Analysis of transformed plants.

The insert of pGNIa1.4 (described below) was subcloned into the plasmid pBluescript KS (Stratagene) and transcripts directed by a T7 promoter were used as probes in hybridization assays of plant material. DNA [Dellaporta, S. L., et al., (1983) Plant Mol. Biol. 1:19–21] and RNA [Chomczynski, P. & Sacchi, N. (1987) Anal. Biochem. 162:156–159] were extracted from leaf tissue. Successful transformation of Km-resistant plants was verified by Southern blot analysis or by DNA-PCR [Saiki, R. K., et al., (1988) Science 239:487–491]. pG3PVY3.9-transformed plants were assayed for expression by Western blot analysis, using CP antibodies. The unavailability of NIa antibodies, however, precluded Western blot analysis in this case. Hence, expression of NIa in transgenic plants was tested by RNA-PCR (reverse transcription coupled with PCR; [Frohman, M. A., et al.,(1988) Proc. Natl. Acad. Sci. USA 85:8998–9002]. The synthetic PCR primers were designed to distinguish between RNA and DNA as described below. The primer sequences were:

Primer #1 (sense): 5' CTATCCTTCGCAAGACCCTTC 3'; (SEQ ID NO: 3);

Primer #10 (sense): 5' TTTGGATCTGCATACAGGAA-GAAAGGG 3'; (SEQ ID NO: 4);

Primer #11 (antisense): 5' CCGACTATACATCCATCG-GCGGTG 3' (SEQ ID NO: 5).

The DNA, either extracted or made from RNA by reverse transcription, was submitted to 30 cycles of PCR: denaturation (45 sec; 94° C.), annealing (45 sec; 60° C.) and extension (60 sec; 72° C.).

Virus assays.

PVY was purified from infected tobacco leaves according to Tanne et al. [Tanne, E., et al., (1977) Phytopathology 67:442–447]. Two leaves per plant were mechanically inoculated with 30 μg/ml PVY (in 10 mM Tris-HCl, pH 7.0). The plants were kept in a growth chamber at 26° C. and inspected daily for symptom appearance. Actual viral accumulation was determined by ELISA. Every four to five days, leaf disks (5 mm in diameter) were removed from the third leaf above the inoculated ones. The leaf disks were homogenized in 1.5-ml microfuge tubes with a teflon pestle (five disks in 500 μl of PBS-Tween-PVP). Sap was applied to a microtiter plate (20 μl/well). Each plate included viral standards, ranging from 1 to 1000 ng/ml PVY. The ELISA assay was performed according to Sela [Sela, I. (1986) Methods in enzymology 119:734–744] using antiserum developed against the purified PVY.

RESULTS

EXAMPLE 1

Cloning of the PVY cistrons and their transfer to plants.

Figure 1:
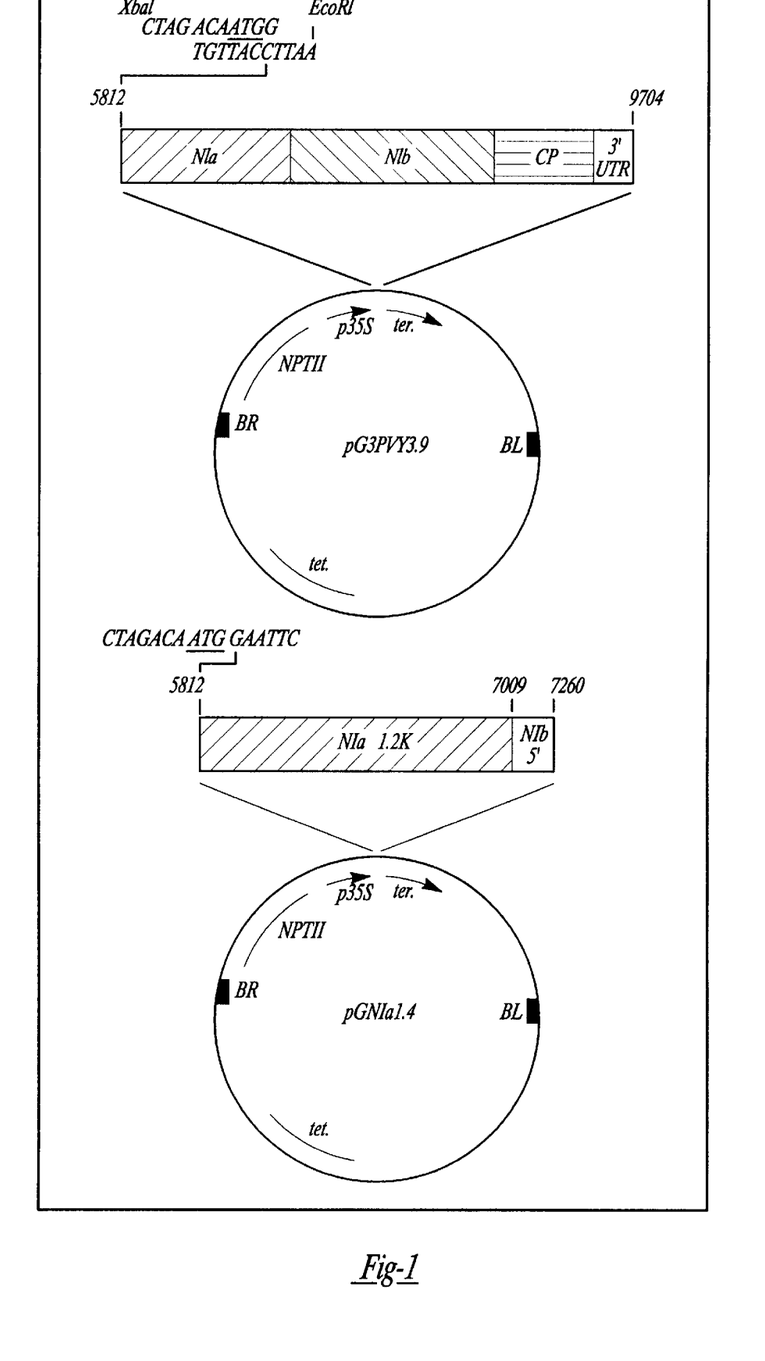

3'PVY3.9 (bases 5812–9704 of PVY) was isolated from the EcoRI fragments of a full-length PVY-cDNA clone [(SEQ ID NO: 2) Karchi, M., et al., (1990) Virus Genes 4:215–224]. PVY1.4 NIa was an EcoRI/BglII fragment of 3'PVY3.9 (bases 5812–7260 of PVY). An oligonucleotide carrying Lutcke's consensus signal for translation initiation in plants (GACAATGG; [Lutcke, H. A., et al., (1987) EMBO J. 6:43–48] between EcoRI and XbaI restriction sites was synthesized and ligated to the EcoRI site of 3'PVY3.9. PVY1.4NIa is a BglII fragment of 3'PVY3.9. The engineered 3'PVY3.9 construct was inserted at the XbaI site of the binary plasmid pGA643, and the engineered construct of PVY1.4NIa was inserted between the XbaI and BglII sites of pGA643. Thus, they were inserted between the 35 S promoter and a terminator, linked to a Km-resistance gene and placed between the border sequences of T-DNA (FIG. 1; ref 13). The engineered binary plasmids (pG3PVY3.9 and pGNIa1.4, respectively) were transferred to *A. tumefaciens* which was then used to transform plants, as described in Materials and Methods.

EXAMPLE 2

Analysis of transformed plants.

Figure 2:
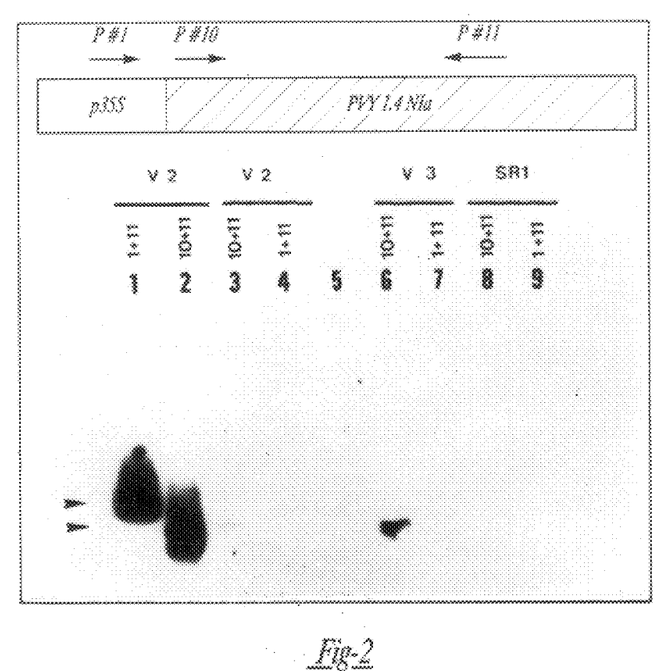
FIG. 2 PCR assays of transgenic plants.

Eighteen out of 25 independently transformed, Km-resistant $R_0$ plants were found to carry PVY1.4NIa as determined by Southern blot analysis (data not shown). Following self-pollination, $R_1$ progeny were selected for Km resistance. Ten $R_1$ progeny of each of six randomly selected $R_0$ plants (total of 60 plants) were further tested. One Km-sensitive $R_1$ plant (NIa$^-$) was also maintained for each of the six independent transformation events, to serve as a negative control descending from the same parent plant. The presence of PVY1.4NIa in $R_1$ plants was assayed by PCR using primers #1 and #11 (FIG. 2). Expression of NIa was tested by RNA-PCR using primers #10 and #11 (FIG. 2A). As a safeguard against possible DNA contamination, a second RNA-PCR, employing primers #1 and #11, was carried out in each case. Since primer #1 represents promoter sequences, any positive PCR band appearing under these conditions would indicate DNA contamination. All individual transformants exhibiting resistance to virus infection, as described below, expressed the NIa cistron (FIG. 2). Expression and processing from pG3PVY3.9-transformed plants is referred to below.

EXAMPLE 3

Assessing protection from PVY infection.

Figure 3:
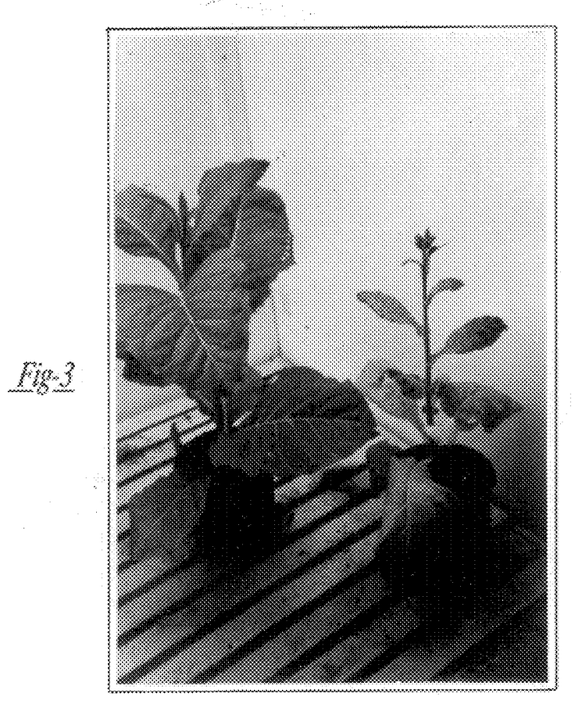
Figure 4A:
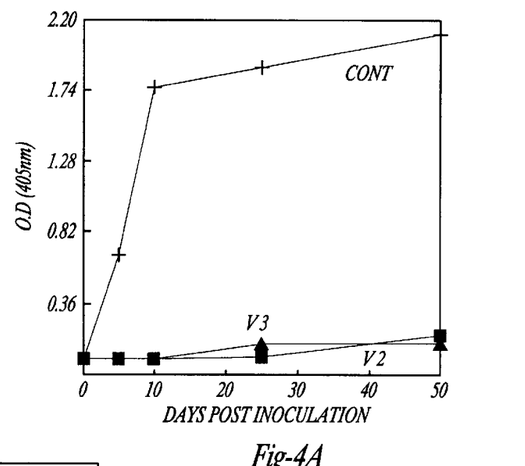
FIG. 4 PVY accumulation in tobacco leaves as determined by ELISA.
Figure 4B:
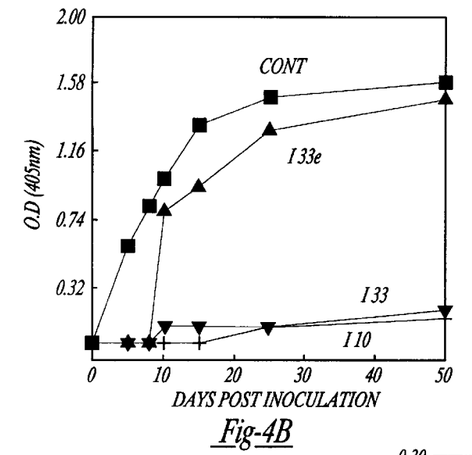
Figure 4C:
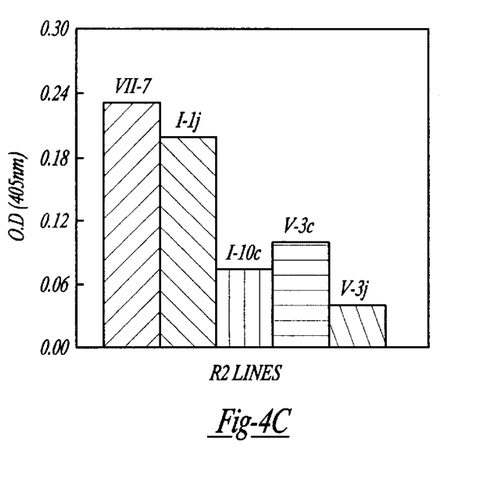

The following tobacco plants were assayed for viral resistance: non-transformed SR1, transformed with an "empty cassette" (insert-less pGA643), $R_1$ transgenic NIa$^+$, and the above-described $R_1$ NIa$^-$-plants. Plants were inoculated with PVY and inspected daily for symptom appearance. Viral accumulation was determined by ELISA at four- to five-day intervals. The $R_1$ progeny of transgenic lines V2 and V3, each carrying two copies of the NPTII gene, and the progeny of V6 carrying a single copy of that gene, were selected for protection studies. As shown in Table 1, all the descendants of V2 and V3 exhibited either partial resistance to viral infection, in which symptom appearance was delayed, or "complete" resistance, where symptoms did not appear at all during the 50-day experimental period (FIG. 3). No viral accumulation could be detected in the resistant plants (FIG. 4). Resistant $R_1$ plants, homozygous for NPTII, were "selfed" and all the desired $R_2$ progeny were resistant.

TABLE 1

Pattern ot symptom appearance in NIa-transformed plants following PVY inoculation.

| Line/day[b] | Percentage of $R_1$ plants[a] showing symptoms | | | | | | | | |
|---|---|---|---|---|---|---|---|---|---|
| | 5 | 6 | 7 | 8 | 10 | 15 | 20 | 25 | 50 |
| SR1[c] | 50 | 100 | | | | | | | |
| Km$^-$; NIa$^{-[d]}$ | 30 | 100 | | | | | | | |
| Km$^+$; NIa$^{-[e]}$ | 50 | 100 | | | | | | | |
| V2[f] | 0 | 0 | 0 | 30 | 40 | 50 | 60 | 60 | 60 |
| V3[f] | 0 | 0 | 20 | 20 | 30 | 30 | 40 | 50 | 50 |
| V6[f] | 0 | 50 | 100 | | | | | | |

[a] 10 $R_1$ plants per line were used for each test
[b] Days after PVY inoculation
[c] Non-transformed piants
[d] Transformed plants, loosing their insert upon segregation
[e] Plants transformed by insert-less pGA643
[f] NIa$^+$ transgenic plants Similar experiments were performed with transgenic plants carrying the NIa-NIb-CP (pG3PVY3.9) construct. Several of these were found to be resistant to PVY according to the criteria used for NIa-transformed plants (an example is shown in FIGS. 3, 4). However, the responsible element for resistance, in this case, is uncertain, since these plants carried also the CP cistron.

Since the only tobacco-infecting potyvirus in Israel is PVY it was not possible to check resistance of the reported transgenic plants to other potyviruses. Resistance to the unrelated virus TMV was, however, tested. Three PVY-resistant V3 (pNIa1.4$^+$) and three PVY-resistant I10 (pG3PVY3.9$^+$) plants were inoculated with 20 μg/ml TMV. Visual observation did not indicate any resistance to TMV, as the severity of symptoms and the time of symptom appearance was similar in the control and the PVY resistant plants.

Several resistant V3 and I10 plants as well as control, non-resistant plants, were kept at 35° C. for 48 hours, then inoculated with PVY two days after that. In this case, very mild symptoms did develop (as compared to severe symptoms in the control plants), with the virus titer in the V3 and I10 plants being less than 40% of that in the control ones (FIG. 4B).

EXAMPLE 4

Assaying the proteolytic activity of the expressed NIa.

Figure 5:
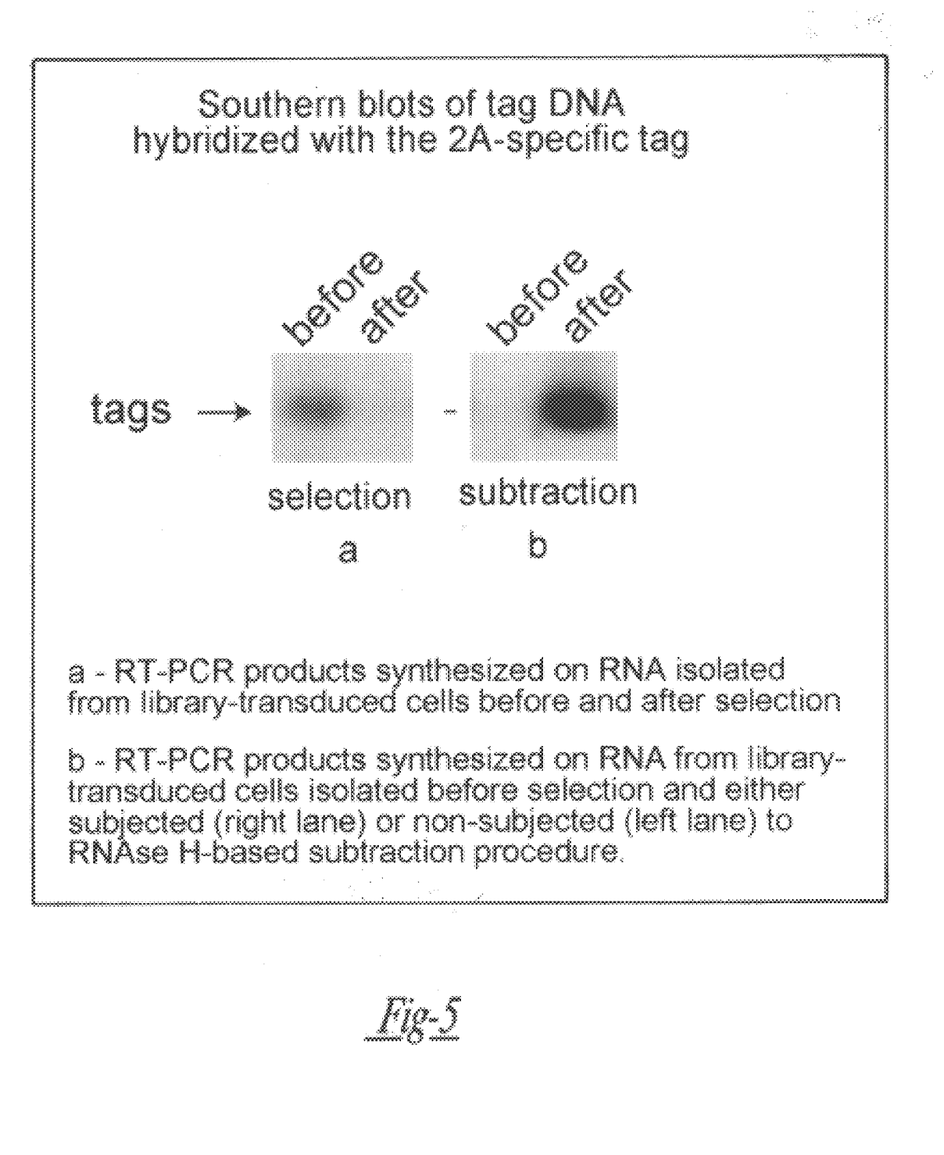

The NIa construct had a 100-base deletion at its 5' end and a 251-base addition at its 3' end. It was therefore of interest to check whether the expressed protein retained its proteolytic activity. Since the NIa-directed protease cleaves at specific sites on the PVY polyprotein, a demonstration of CP processing would provide evidence of its activity. Therefore, tobacco plants were transformed with pG3PVY3.9 (caryying the PVY segment NIa-NIb-CP) and selected as described above. Protein was extracted therefrom and the presence of PVY-CP was checked by Western blot analysis. FIG. 5 demonstrates that mature CP (33 KDa) was indeed expressed in these transgenic plants, thereby indicating NIa proteolytic activity. This was corroborated by the detection of processing intermediary products as well. Several other bands reacted with the antibody, and the two bands that reacted most strongly were of the size expected for the intermediary products during processing (126 KDa and 82 KDa). These proteins migrated somewhat slower than the corresponding non-specific bands of the control plants. The pattern of CP-related proteins in these transgenic plants was identical to that detected in PVY-infected plants, indicating correct processing. It is noteworthy that an almost complete processing took place in the PVY-infected plants, and very little intermediary products were detected, while the transgenic plants exhibited very little mature CP, and a larger proportion of the intermediary proteins. Nevertheless, the expressed product of the cloned NIa retained its native proteolytic activity.

We claim:

1. A chimeric plasmid comprising at least one non-structural potyvirus gene encoding potyvirus protease selected from the group consisting of SEQ ID No: 1 and SEQ ID No: 2, which gene is capable of being expressed in a plant transformed with the chimeric plasmid, the thus transformed plant being resistant to an infection by a plant potyvirus.

2. A chimeric plasmid according to claim 1 wherein said chimeric plasmid comprises a DNA sequence encoding potyvirus protease, replicase and coat protein.

3. A chimeric plasmid according to claim 1 wherein said potyvirus gene is the potyvirus sequence NIa1.4 (SEQ ID No: 1) wherein said sequence at the 5' end carries a plant ribosomal binding site sequence CTAGACAATG linked to the PVY gene by a restriction site.

4. A chimeric plasmid according to claim 2 wherein said DNA sequence is the potyvirus sequence 3'PVY3.9 (SEQ ID No: 2) wherein said sequence at the 5' end carries a plant ribosomal binding site sequence CTAGACAATG linked to the PVY gene by a restriction site.

5. A chimeric plasmid according to claim 1 further comprising at least one genetic control element.

6. A chimeric plasmid according to claim 5 wherein said genetic control element is selected from the group consisting of promoters, enhancers and terminators.

7. A chimeric plasmid according to claim 1 wherein said potyvirus gene can replicate in *E. coli*.

8. A chimeric plasmid according to claim 7 wherein said plasmid is pBluescript KS.

9. A chimeric plasmid according to claim 1 comprising said at least one non-structural potyvirus gene in a suitable binary plasmid.

10. A chimeric plasmid according to claim 9 comprising at least one genetic control element.

11. A chimeric plasmid according to claim 10 wherein said genetic control element is selected from the group consisting of promoters, enhancers and terminators.

12. A chimeric plasmid according to claim 11 wherein said binary plasmid comprises a plant promotor region and two tandem nos termination signals in opposite orientation.

13. A chimeric plasmid according to claim 12 wherein said binary plasmid is pGA643.

14. A chimeric plasmid according to claim 13 wherein said potyvirus gene is the potyvirus sequence NIa1.4 (SEQ ID NO: 1).

15. A chimeric plasmid according to claim 14 wherein said NIa1.4 sequence (SEQ ID NO: 1) is inserted at the XbaI site of the binary plasmid pGA643.

16. A chimeric plasmid according to claim 13 wherein said potyvirus gene is the potyvirus sequence 3'PVY3.9 (SEQ ID NO: 2).

17. A chimeric plasmid according to claim 16 wherein said 3'PVY3.9 sequence (SEQ ID NO: 1) is inserted between the XbaI and BglII sites of the binary plasmid pGA643.

18. A microorganism transformed with at least one chimeric plasmid according to claim 1.

19. A microorganism according to claim 18 wherein said microorganism is *E. coli*.

20. A microorganism according to claim 18 wherein said microorganism is an Agrobacterium.

21. A microorganism according to claim 20 wherein said microorganism is an *Agrobacterium tumefaciens*.

22. A potyvirus-resistant plant having cells containing in their genomes a non-structural potyvirus gene incorporated into the plant via a chimeric plasmid according to claim 1.

23. A seed of a potyvirus resistant plant according to claim 22.

24. A cell of a potyvirus resistant plant according to claims 22.

25. A plant cell culture consisting of cells acording to claim 24.

26. A method of protecting plants against potyvirus infection wherein genomes of cells of the plant are provided with a potyvirus non-structural gene incorporated thereinto via a chimeric plasmid according to claim 1, whereby the cells become resistant to an infection by a potyvirus wherein the genome of said seed comprises the sequence of SEQ ID NO: 1 or SEQ ID NO: 2.

* * * * *